United States Patent
Burnett et al.

(10) Patent No.: US 6,312,945 B1
(45) Date of Patent: Nov. 6, 2001

(54) HUMAN GLUTAMATE RECEPTOR PROTEINS AND ASSOCIATED DNA COMPOUNDS

(75) Inventors: J. Paul Burnett; Nancy G. Mayne; Robert L. Sharp; Yvonne M. Snyder, all of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/400,067

(22) Filed: Mar. 7, 1995

Related U.S. Application Data

(62) Division of application No. 07/885,912, filed on May 19, 1992, now abandoned.

(51) Int. Cl.[7] ........................... C12N 15/12; C12N 15/63; C07K 14/705
(52) U.S. Cl. ..................... 435/320.1; 435/69.1; 435/325; 435/440; 435/70.3; 536/23.5
(58) Field of Search ................................. 536/23.5, 23.1; 435/320.1, 69.1, 240.2, 252.3, 70.3, 172.3, 325, 440; 935/4, 11, 27, 71, 70

(56) References Cited

FOREIGN PATENT DOCUMENTS

WO/91/06648   5/1991  (WO) .

OTHER PUBLICATIONS

D.K. Grandy et al. "Cloning of the cDNA and Gene for a Human D2 Dopamine Receptor", Proc. Natl. Acad. Sci. 86: 9762–9766, Dec. 1989.*

N.P. Gerard et al., The Human Neurokinin A (Substance K) Receptor, J. Biol. Chem. 265(33): 20455–20462, Nov. 1990.*

Q.Y. Zhou et al., "Cloning and Expression of Human and Rat D1 Dopamine Receptors", Nature 347: 76–80, Sep. 1990.*

S.L. Berger et al., "Guide to Molecular Cloning Techniques", Meth. Enzymol. 152: 393–399, 415–423, 432–447, 663–704, 1987.*

Sommer, B., et al., *Science*, vol. 249, 1990, pp. 1580–1585.

Boulter, et al., "Molecular Cloning and Functional expression at Glutamate Receptor Subunit Genes", Science 249: 1033–1037 (1990).

Hollman, et al., Cloning by Functional Expression of a Member of the Glutamate Receptor Family, Nauture, 342, 643–648 (Dec. 1989).

Puckett, C. et al., *Proc. Natl. Acad. Sci.*, 7557 (1991).

Sun W. et al., *89 Proc. Natl. Acad. Sci.*, 1443 (1992).

Unwin N., 3 *Neuron* 665 (1989).

Keinanen K. et al., 249 *Science* 556 (1990).

Sakimura K. et al., *272 FEBS Lett.* 73 (1990).

Werner P. et al., *341 Nature* 742 (1991).

Bettler B. et al., 8 *Neuron* 257 (1992).

* cited by examiner

*Primary Examiner*—Rebecca E. Prouty
(74) *Attorney, Agent, or Firm*—Alexander Wilson; Paul J. Gaylo

(57) ABSTRACT

The present invention provides a human glutamate receptor and related DNA compounds useful not only in assays for potential pharmaceuticals but also in methods for molecular biology techniques.

7 Claims, No Drawings

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 883 amino acids
      (B) TYPE: amino acid
      (D) TOPOLOGY: linear (ii) MOLECULE TYPE: protein (xi) SEQUENCE DESCRIPTION: SEQ ID NO:1:

```
Met Gln Lys Ile Met His Ile Ser Val Leu Leu Ser Pro Val Leu Trp
 1               5                  10                  15

Gly Leu Ile Phe Gly Val Ser Ser Asn Ser Ile Gln Ile Gly Gly Leu
                20                  25                  30

Phe Pro Arg Gly Ala Asp Gln Glu Tyr Ser Ala Phe Arg Val Gly Met
            35                  40                  45

Val Gln Phe Ser Thr Ser Glu Phe Arg Leu Thr Pro His Ile Asp Asn
 50                  55                  60

Leu Glu Val Ala Asn Ser Phe Ala Val Thr Asn Ala Phe Cys Ser Gln
65                  70                  75                  80

Phe Ser Arg Gly Val Tyr Ala Ile Phe Gly Phe Tyr Asp Lys Lys Ser
                85                  90                  95

Val Asn Thr Ile Thr Ser Phe Cys Gly Thr Leu His Val Ser Phe Ile
                100                 105                 110

Thr Pro Ser Phe Pro Thr Asp Gly Thr His Pro Phe Val Ile Gln Met
            115                 120                 125

Arg Pro Asp Leu Lys Gly Ala Leu Leu Ser Leu Ile Glu Tyr Tyr Gln
        130                 135                 140

Trp Asp Lys Phe Ala Tyr Leu Tyr Asp Ser Asp Arg Gly Leu Ser Thr
```

```
                                        -continued
145                 150                 155                 160

Leu Gln Ala Val Leu Asp Ser Ala Glu Lys Lys Trp Gln Val Thr
                165                 170                 175

Ala Ile Asn Val Gly Asn Ile Asn Asn Asp Lys Lys Asp Glu Met Tyr
                180                 185                 190

Arg Ser Leu Phe Gln Asp Leu Glu Leu Lys Lys Glu Arg Arg Val Ile
        195                 200                 205

Leu Asp Cys Glu Arg Asp Lys Val Asn Asp Ile Val Asp Gln Val Ile
    210                 215                 220

Thr Ile Gly Lys His Val Lys Gly Tyr His Tyr Ile Ile Ala Asn Leu
225                 230                 235                 240

Gly Phe Thr Asp Gly Asp Leu Leu Lys Ile Gln Phe Gly Gly Ala Asn
                245                 250                 255

Val Ser Gly Phe Gln Ile Val Asp Tyr Asp Asp Ser Leu Val Ser Lys
                260                 265                 270

Phe Ile Glu Arg Trp Ser Thr Leu Glu Glu Lys Glu Tyr Pro Gly Ala
            275                 280                 285

His Thr Thr Thr Ile Lys Tyr Thr Ser Ala Leu Thr Tyr Asp Ala Val
        290                 295                 300

Gln Val Met Thr Glu Ala Phe Arg Asn Leu Arg Lys Gln Arg Ile Glu
305                 310                 315                 320

Ile Ser Arg Arg Gly Asn Ala Gly Asp Cys Leu Ala Asn Pro Ala Val
                325                 330                 335

Pro Trp Gly Gln Gly Val Glu Ile Glu Arg Ala Leu Lys Gln Val Gln
                340                 345                 350

Val Glu Gly Leu Ser Gly Asn Ile Lys Phe Asp Gln Asn Gly Lys Arg
        355                 360                 365

Ile Asn Tyr Thr Ile Asn Ile Met Glu Leu Lys Thr Asn Gly Pro Arg
    370                 375                 380

Lys Ile Gly Tyr Trp Ser Glu Val Asp Lys Met Val Val Thr Leu Thr
385                 390                 395                 400

Glu Leu Pro Ser Gly Asn Asp Thr Ser Gly Leu Glu Asn Lys Thr Val
                405                 410                 415

Val Val Thr Thr Ile Leu Glu Ser Pro Tyr Val Met Met Lys Lys Asn
                420                 425                 430

His Glu Met Leu Glu Gly Asn Glu Arg Tyr Glu Gly Tyr Cys Val Asp
        435                 440                 445

Leu Ala Ala Glu Ile Ala Lys His Cys Gly Phe Lys Tyr Lys Leu Thr
    450                 455                 460

Ile Val Gly Asp Gly Lys Tyr Gly Ala Arg Asp Ala Asp Thr Lys Ile
465                 470                 475                 480

Trp Asn Gly Met Val Gly Glu Leu Val Tyr Gly Lys Ala Asp Ile Ala
                485                 490                 495

Ile Ala Pro Leu Thr Ile Thr Leu Val Arg Glu Glu Val Ile Asp Phe
                500                 505                 510

Ser Lys Pro Phe Met Ser Leu Gly Ile Ser Ile Met Ile Lys Lys Pro
        515                 520                 525

Gln Lys Ser Lys Pro Gly Val Phe Ser Phe Leu Asp Pro Leu Ala Tyr
    530                 535                 540

Glu Ile Trp Met Cys Ile Val Phe Ala Tyr Ile Gly Val Ser Val Val
545                 550                 555                 560

Leu Phe Leu Val Ser Arg Phe Ser Pro Tyr Glu Trp His Thr Glu Glu
                565                 570                 575
```

```
Phe Glu Asp Gly Arg Glu Thr Gln Ser Ser Glu Ser Thr Asn Glu Phe
            580                 585                 590

Gly Ile Phe Asn Ser Leu Trp Phe Ser Leu Gly Ala Phe Met Arg Gln
            595                 600                 605

Gly Cys Asp Ile Ser Pro Arg Ser Leu Ser Gly Arg Ile Val Gly Gly
            610                 615                 620

Val Trp Trp Phe Phe Thr Leu Ile Ile Ile Ser Ser Tyr Thr Ala Asn
625                 630                 635                 640

Leu Ala Ala Phe Leu Thr Val Glu Arg Met Val Ser Pro Ile Glu Ser
                    645                 650                 655

Ala Glu Asp Leu Ser Lys Gln Thr Glu Ile Ala Tyr Gly Thr Leu Asp
                    660                 665                 670

Ser Gly Ser Thr Lys Glu Phe Phe Arg Arg Ser Lys Ile Ala Val Phe
                    675                 680                 685

Asp Lys Met Trp Thr Tyr Met Arg Ser Ala Glu Pro Ser Val Phe Val
                    690                 695                 700

Arg Thr Thr Ala Glu Gly Val Ala Arg Val Arg Lys Ser Lys Gly Lys
705                 710                 715                 720

Tyr Ala Tyr Leu Leu Glu Ser Thr Met Asn Glu Tyr Ile Glu Gln Arg
                    725                 730                 735

Lys Pro Cys Asp Thr Met Lys Val Gly Gly Asn Leu Asp Ser Lys Gly
                    740                 745                 750

Tyr Gly Ile Ala Thr Pro Lys Gly Ser Ser Leu Arg Thr Pro Val Asn
                    755                 760                 765

Leu Ala Val Leu Lys Leu Ser Glu Gln Gly Val Leu Asp Lys Leu Lys
                    770                 775                 780

Asn Lys Trp Trp Tyr Asp Lys Gly Glu Cys Gly Ala Lys Asp Ser Gly
785                 790                 795                 800

Ser Lys Glu Lys Thr Ser Ala Leu Ser Leu Ser Asn Val Ala Gly Val
                    805                 810                 815

Phe Tyr Ile Leu Val Gly Gly Leu Gly Leu Ala Met Leu Val Ala Leu
                    820                 825                 830

Ile Glu Phe Cys Tyr Lys Ser Arg Ala Glu Ala Lys Arg Met Lys Val
                    835                 840                 845

Ala Lys Asn Ala Gln Asn Ile Asn Pro Ser Ser Ser Gln Asn Ser Gln
850                 855                 860

Asn Phe Ala Thr Tyr Lys Glu Gly Tyr Asn Val Tyr Gly Ile Glu Ser
865                 870                 875                 880

Val Lys Ile (2) INFORMATION FOR SEQ ID NO:2:

(i) SEQUENCE CHARACTERISTICS:
        (A) LENGTH: 2649 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:2:

ATGCAAAAGA TTATGCATAT TTCTGTCCTC CTTTCTCCTG TTTTATGGGG ACTGATTTTT      60

GGTGTCTCTT CTAACAGCAT ACAGATAGGG GGGCTATTTC CTAGGGGCGC CGATCAAGAA     120

TACAGTGCAT TTCGAGTAGG GATGGTTCAG TTTTCCACTT CGGAGTTCAG ACTGACACCC     180
```

```
CACATCGACA ATTTGGAGGT GGCAAACAGC TTCGCAGTCA CTAATGCTTT CTGCTCCCAG    240

TTTTCGAGAG GAGTCTATGC TATTTTTGGA TTTTATGACA AGAAGTCTGT AAATACCATC    300

ACATCATTTT GCGGAACACT CCACGTCTCC TTCATCACTC CCAGCTTCCC AACAGATGGC    360

ACACATCCAT TTGTCATTCA GATGAGACCC GACCTCAAAG GAGCTCTCCT TAGCTTGATT    420

GAATACTATC AATGGGACAA GTTTGCATAC CTCTATGACA GTGACAGAGG CTTATCAACA    480

CTGCAAGCTG TGCTGGATTC TGCTGCTGAA AGAAATGGC AAGTGACTGC TATCAATGTG    540

GGAAACATTA ACAATGACAA GAAAGATGAG ATGTACCGAT CACTTTTTCA AGATCTGGAG    600

TTAAAAAAGG AACGGCGTGT AATTCTGGAC TGTGAAAGGG ATAAAGTAAA CGACATTGTA    660

GACCAGGTTA TTACCATTGG AAAACATGTT AAAGGGTACC ACTACATCAT TGCAAATCTG    720

GGATTTACTG ATGGAGACCT ATTAAAAATC CAGTTTGGAG GTGCAAATGT CTCTGGATTT    780

CAGATAGTGG ACTATGATGA TTCGTTGGTA TCTAAATTTA TAGAAAGATG GTCAACACTG    840

GAAGAAAAAG AATACCCTGG AGCTCACACA ACAACAATTA AGTATACTTC TGCTCTGACC    900

TATGATGCCG TTCAAGTGAT GACTGAAGCC TTCCGCAACC TAAGGAAGCA AAGAATTGAA    960

ATCTCCCGAA GGGGGAATGC AGGAGACTGT CTGGCAAACC CAGCAGTGCC CTGGGGACAA   1020

GGTGTAGAAA TAGAAAGGGC CCTCAAACAG GTTCAGGTTG AAGGTCTCTC AGGAAATATA   1080

AAGTTTGACC AGAATGGAAA AAGAATAAAC TATACAATTA ACATCATGGA GCTCAAAACT   1140

AATGGGCCCC GGAAGATTGG CTACTGGAGT GAAGTGGACA AAATGGTTGT TACCCTTACT   1200

GAGCTCCCTT CTGGAAATGA CACCTCTGGG CTTGAGAATA GACTGTTGT TGTCACCACA   1260

ATTTTGGAAT CTCCGTATGT TATGATGAAG AAAAATCATG AAATGCTTGA AGGCAATGAG   1320

CGCTATGAGG GCTACTGTGT TGACCTGGCT GCAGAAATCG CCAAACATTG TGGGTTCAAG   1380

TACAAGTTGA CAATTGTTGG TGATGGCAAG TATGGGGCCA GGGATGCAGA CACGAAAATT   1440

TGGAATGGGA TGGTTGGAGA ACTTGTATAT GGGAAAGCTG ATATTGCAAT TGCTCCATTA   1500

ACTATTACCC TTGTGAGAGA AGAGGTGATT GACTTCTCAA AGCCCTTCAT GAGCCTCGGG   1560

ATATCTATCA TGATCAAGAA GCCTCAGAAG TCCAAACCAG GAGTGTTTTC CTTTCTTGAT   1620

CCTTTAGCCT ATGAGATCTG GATGTGCATT GTTTTTGCCT ACATTGGGGT CAGTGTAGTT   1680

TTATTCCTGG TCAGCAGATT TAGCCCCTAC GAGTGGCACA CTGAGGAGTT TGAAGATGGA   1740

AGAGAAACAC AAAGTAGTGA ATCAACTAAT GAATTTGGGA TTTTTAATAG TCTCTGGTTT   1800

TCCTTGGGTG CCTTTATGCG GCAAGGATGC GATATTTCGC CAAGATCCCT CTCTGGGCGC   1860

ATTGTTGGAG GTGTGTGGTG GTTCTTTACC CTGATCATAA TCTCCTCCTA CACGGCTAAC   1920

TTAGCTGCCT TCCTGACTGT AGAGAGGATG GTGTCTCCCA TCGAAAGTGC TGAGGATCTT   1980

TCTAAGCAAA CAGAAATTGC TTATGGAACA TTAGACTCTG GCTCCACTAA AGAGTTTTTC   2040

AGGAGATCTA AAATTGCAGT GTTTGATAAA ATGTGGACCT ACATGCGGAG TGCGGAGCCC   2100

TCTGTGTTTG TGAGGACTAC GGCCGAAGGG GTGGCTAGAG TGCGGAAGTC CAAAGGGAAA   2160

TATGCCTACT TGTTGGAGTC CACGATGAAC GAGTACATTG AGCAAAGGAA GCCTTGCGAC   2220

ACCATGAAAG TTGGTGGAAA CCTGGATTCC AAAGGCTATG GCATCGCAAC ACCTAAAGGA   2280

TCCTCATTAA GAACCCCAGT AAATCTTGCA GTATTGAAAC TCAGTGAGCA AGGCGTCTTA   2340

GACAAGCTGA AAAACAAATG GTGGTACGAT AAAGGTGAAT GTGGAGCCAA GGACTCTGGA   2400

AGTAAGGAAA AGACCAGTGC CCTCAGTCTG AGCAACGTTG CTGGAGTATT CTACATCCTT   2460

GTCGGGGGCC TTGGTTTGGC AATGCTGGTG GCTTTGATTG AGTTCTGTTA CAAGTCAAGG   2520

GCCGAGGCGA AACGAATGAA GGTGGCAAAG AATGCACAGA ATATTAACCC ATCTTCCTCG   2580
```

```
CAGAATTCAC AGAATTTTGC AACTTATAAG GAAGGTTACA ACGTATATGG CATCGAAAGT        2640

GTTAAAATT                                                               2649
```

(2) INFORMATION FOR SEQ ID NO:3:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:3:

```
ATGCAAAAGA TTATGCATAT TTCTGTCCTC CTTTCTCCTG TTTTATGGGG ACTGATTTTT         60
```

(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:4:

```
GTAGGGATGG TTCAGTTTTC CACTTCGGAG TTCAGACTGA CACCCCACAT CGACAATTTG         60
```

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:5:

```
AATTTTGCAA CTTATAAGGA AGGTTACAAC GTATATGGCA TCGAAAGTGT TAAAATTTAA         60
```

HUMAN GLUTAMATE RECEPTOR PROTEINS AND ASSOCIATED DNA COMPOUNDS

This application is a division of application Ser. No. 07/885,912, filed May 19, 1992 now abandoned.

BACKGROUND OF THE INVENTION

In the mammalian central nervous system, L-glutamate serves as a major excitatory neurotransmitter. The interaction of glutamate with its membrane-bound receptors is believed to play a role in many important neuronal processes, including, for example, fast synaptic transmission, synaptic plasticity and long-term potentiation. These processes are fundamental to the maintenance of life and normal human abilities such as learning and memory. Monaghan D. T. et al., 8 Neuron 267 (1992).

Pharmacological characterization of receptors for L-glutamate has led to their classification into two families based on their biological function: the ionotropic receptors which are directly coupled to cation channels in the cell membrane, and the metabotropic receptors which function through coupling to G-proteins. A number of ionotropic receptors have been further characterized on the basis of the relatively specific agonists by which they can be activated. One major group comprises those receptors activated by N-methyl-D-aspartate (NMDA), which appears to have multiple allosteric modulatory sites. The other two groups consist of those receptors activated by kainate and/or amino-3-hydroxy-5-methyl-4-isoxozole propionate (AMPA). Collingridge G. L. et al., 40 Pharmacol. Rev. 143 (1989).

Molecular cloning studies of rodent ionotropic receptors have recently provided some information on the molecular structure of these proteins. The cDNAs for seven different subtypes of the kainate/AMPA group have been characterized. Heinemann S. et al., PCT publication, WO91/06648 (1991), Keinanen K. et al., 249 Science 556 (1990), Sakimura K. et al., 272 FEBS Lett. 73 (1990), Werner P. et al., 341 Nature 742 (1991), Bettler B. et al., 8 Neuron 257 (1992). Splice variants, referred to as "flip" and "flop", of same of these have been characterized as well. Sommer B. et al., 249 Science 1580 (1990). In addition, two members of the NMDA group have been cloned. Moriyoshi, K. et al., 354 Nature 31 (1991) and Meguro H. et al., 357 Nature 70 (1992). An NMDA-related protein has also been reported. Kumar K. N. et al., 354 Nature 70 (1991). These proteins share varying degrees of homology with one another and are therefore believed to represent a gene superfamily. Based on analogy with other better characterized ion channel receptors, glutamate ionotropic receptors are expected to exist in vivo within the cell membrane as heteromeric multisubunit assemblies of these subunits. Unwin N., 3 Neuron 665 (1989).

Moreover, at least two human glutamate receptors have been reported as cloned. Puckett C. et al., 88 Proc. Nat. Acad. Sci. 7557 (1991) and Sun W. et al., 89 Proc. Nat. Acad. Sci. 1443 (1992). The glutamate receptor cloned by Puckett et al. was named GluHI and was later identified to be the "flip" version of this particular receptor. The Sun W. et al. reference refers to the glutamate receptor they cloned as the HBGR1 receptor and explains that HBGR1 is presumed the "flop" version of GluHI. Sun et al. also discloses the possible existence of, but does not describe in detail, a partial clone of HBGR2, or human GluR2.

In addition to its role in normal human physiology, interaction of L-glutamate with its receptors is believed to play a key role in many neurological disorders such as stroke, epilepsy and head trauma, as well as neurodegenerative processes such as Alzheimer's disease. Olney R. W., 17 Drug Dev. Res., 299 (1989). For this reason, understanding the molecular structure of human L-glutamate receptors will be important for understanding these disease processes as well as for furthering the search for effective therapeutic agents. Up to the present, the search for therapeutic agents which will selectively bind and modulate the function of human glutamate receptors has been hampered by the unavailability of homogeneous sources of receptors to use for screens and tests of potential drug candidate compounds. The brain tissues commonly used by pharmacologists presently are derived from experimental animals (non-human) and furthermore contain mixtures of various types of glutamate receptors.

In searching for drugs for human therapy it is desirable to use receptors that are more analogous to those in the intact human brain than are the rodent receptors employed to date. The current invention provides a human receptor and functional equivalents thereof which can be used to search for drugs which modulate this receptor.

For purposes of clarity and as an aid in understanding the invention, as disclosed and claimed herein, the following items are defined below.

"Functional HSG1uR2"—A compound comprising SEQ ID NO:1 which, when alone or combined with another glutamate receptor, is capable of generating ion flow, binding glutamate, interacting with glutaminergic ligand, or performing in a manner consistent with a glutamate receptor.

"GluR2 receptor"—The amino acid sequence commonly associated with the rat ionotropic glutamate receptor 2.

"GluR3 receptor"—The amino acid sequence commonly associated with the rat ionotropic glutamate receptor 3.

"HSG1uR1 receptor"—The amino acid compound disclosed in copending application (attorney docket No. 8342, having inventors Burnett J. P., Mayne N. G., Sharp R. L. and Snyder Y. M.) or functional equivalents thereof.

"HSG1uR2 receptor"—The compound having amino acid sequence SEQ ID NO:1 or functional equivalents thereof.

"mRNA"—RNA which has been transcribed either in vivo or in vitro, including, for example, RNA transcripts prepared in vitro via transcription of coding sequences of DNA by RNA polymerase.

"Part of SEQ ID NO:1"—A sequence containing at least 6 consecutive amino acid residues or more and that corresponds to a sequence contained in SEQ ID NO:1.

"Physically detectable"—Any information which has been presented in humanly recognizable form, with or without the aid of intervening interpretation. For example, electrophysiological, chemical or biochemical data is considered within the realm of physically detectable information.

"Primer"—A nucleic acid fragment or its reverse complement which functions as template for enzymatic or synthetic elongation.

"Probe"—A nucleic acid compound or a fragment thereof, or their reverse complement, either of which is used to hybridize to other nucleic acids.

"SEQ ID NO:1 and functional equivalents thereof"—SEQ ID NO:1 and conservative alterations of the amino acid sequence of SEQ ID NO:1, wherein the conservative alterations result in a compound which exhibits substantially the same biological, biochemical, physical and structural qualities of SEQ ID:1.

"SEQ ID NO:2"—a DNA sequence which encodes SEQ ID NO:1.

"SEQ ID NO:3"—The DNA sequence ATGCAAAAGA TTATGCATAT TTCTGTCCTC CTTTCTCCTG TTT-TATGGGG ACTGATTTT. This segment includes bases 1 through 60 of SEQ ID NO:2, counting from the 5' end.

"SEQ ID NO:4"—The DNA sequence GTAGG GATGG TTCAGTTTTC CACTTCGGAG TTCAGACTGA CAC-CCCACAT CGACAATTTG. This segment includes bases 136 through 195 of SEQ ID NO:2, counting from the 5' end.

"SEQ ID NO:5"—The DNA sequence AATTTTGCAA CTTATAAGGA AGGTTACAAC GTATATGGCA TCGAAAGTGT TAAAATTTAA. This segment includes bases 2593 through 2649 of SEQ ID NO:2, with a TAA stop codon added at the 3' end.

"Transfection"—Any transfer of nucleic acid into a host cell, with or without integration of said nucleic acid into genome of said host cell.

SUMMARY OF THE INVENTION

The present invention provides amino acid compounds which comprise the amino acid sequence SEQ ID NO:1, and functional equivalents thereof. In particular, the amino acid compound which is SEQ ID NO:1 is preferred.

The invention also provides nucleic acid compounds which comprise a nucleic acid sequence which encodes the amino acid compounds provided. Particularly, nucleic acid compounds which are DNA are preferred. Most preferred is the DNA compound SEQ ID NO:2. However, also preferred are those nucleic acid compounds which are sense mRNA.

Also provided by the present invention are nucleic acid vectors comprising nucleic acids which encode SEQ ID NO:1 or functional equivalents thereof. Preferred nucleic acid vectors are those which are DNA. Most preferred are DNA vectors which comprise SEQ ID NO:2. The DNA vector most preferred is plasmid pRS113.

Restriction fragments of the preferred vector are also provided. Particularly, the approximately 2.9 kb (kilobase) AlwnI/SalI restriction fragment and the approximately 2.9 EcoRI restriction fragment of pRS113 are provided.

Moreover, DNA vectors of the present invention preferably comprise a promoter positioned to drive expression of said DNA sequence. A preferred DNA expression vector is one wherein the promoter functions in mammalian cells. A more preferred DNA expression vector is one wherein the promoter functions in COS-7 cells. Most preferred COS-7 DNA expression vectors comprise SEQ ID NO:2.

The present invention also provides probes and primers useful for molecular biology techniques. Compounds which encode SEQ ID NO:1 or a part thereof and which are at least 18 consecutive base pairs in length are provided. Preferably, the 18 base pair or more compound is DNA. Most preferred for this use are the DNA compounds which are SEQ ID NO:3, SEQ ID NO:4 and SEQ ID NO:5.

Further, this invention provides cells in which the nucleic acid compounds of the invention may be harbored. For example, oocytes which comprise a nucleic acid compound which encodes all or part of SEQ ID NO:1 are provided. Oocytes wherein DNA expresses HSG1uR2 receptor are preferred. Most preferred are oocytes wherein sense mRNA expresses HSG1uR2 receptor.

Moreover, oocytes wherein nucleic acid compounds of the invention express functional HSG1uR2 receptor are provided. For example, oocytes wherein nucleic acid compounds of the invention express functional HSG1uR2/HSG1uR1 complex are provided. Oocytes wherein nucleic acids of the present invention express functional HSG1uR2/HSG1uR1 complex and wherein GluR3 receptor is also expressed are provided. Oocytes which comprise functional HSG1uR2 and which further comprise GluR1 receptor are part of the present invention. Furthermore, oocytes which comprise functional HSG1uR2 and which further comprise GluR3 receptor are also provided. Oocytes which comprise functional HSG1uR2 receptor and wherein GluR1 receptor is co-expressed, and wherein GluR3 receptor is additionally expressed are also provided.

Other host cells provided by the present invention include those which are transfected with a nucleic acid compound which encodes SEQ ID NO:1 or functional equivalents thereof. Preferred cells include host cells transfected with a DNA vector. Host cells wherein the DNA vector comprises the DNA sequence SEQ ID NO:2 are preferred. Preferred transfected host cells which encode SEQ ID NO:2 are *E. coli* cells. The most preferred *E. coli* host cell is *E. coli*/pRS113.

Host cells wherein a DNA expression vector encodes HSG1uR2 receptor are also provided. Preferably, the DNA vector comprises SEQ ID NO:2. Preferred host cells for expression of HSG1uR2 are mammalian cells. Preferred mammalian cells for expression of HSG1uR2 are COS-7 cells.

Specifically, host cells which have been transfected with a DNA expression vector which expresses functional HSG1uR2 receptor are provided. Host cells which have been transfected with a DNA expression vector which expresses functional HSG1uR2/HSG1uR1 complex are also provided. Host cells which have been transfected with a DNA expression vector which expresses functional HSG1uR2/HSG1uR1 complex and which further comprise a DNA vector which encodes a GluR3 receptor are provided. Host cells which comprise a DNA vector which encodes HSG1uR2 receptor which further comprises a vector encoding GluR1 receptor is also provided. Likewise, host cells which comprise a DNA vector which encodes HSG1uR2 receptor which further comprises a vector encoding GluR3 receptor are provided. Moreover, host cells which comprise a DNA expression vector which expresses HSG1uR2 receptor, and which further comprise a DNA vector which encodes a GluR1 receptor, and which further comprise a DNA vector which encodes a GluR3 receptor are also provided.

Additionally, the invention provides a method for identifying DNA homologous to a probe of the present invention, which comprises contacting test nucleic acid with the probe under hybridizing conditions and identifying test nucleic acids which hybridize. The preferred method utilizes SEQ ID NO:3, SEQ ID NO:4 or SEQ ID NO:5 as probes.

Assays utilizing the compounds provided by the present invention are also provided. These assays determine whether a substance interacts with or affects HSG1uR2, said assay comprising introducing the substance and functional HSG1uR2 into an acceptable medium, and monitoring interaction by physically detectable means, thereby identifying those substances which interact with or affect HSG1uR2. Preferred assays include those which utilize both HSG1uR2 and HSG1uR1 receptor, and which results in a functional HSG1uR2/HSG1uR1 complex. Assays provided include those which utilize both functional HSG1uR2/HSG1uR1 complex and GluR3 receptor. Other assays include those which utilize HSG1uR2 and GluR1 receptor or HSG1uR2 and GluR3 receptor. Another assay utilizes HSG1uR2 and both a GluR1 receptor and a GluR3 receptor.

Preferably, the physically detectable means is selected from 1) competing with labeled glutamate, 2) interacting with glutaminergic ligand or 3) generating ion flow. A preferred assay is an oocyte assay system. A most preferred competition assay system utilizes radioactively-labeled glutamate. A most preferred oocyte assay system utilizes sense mRNA.

The invention also provides a method for constructing a host cell capable of expressing a nucleic acid compound which encodes a compound which comprises SEQ ID NO:1 or functional equivalents thereof, said method comprising transfecting a host cell with a DNA vector which comprises said nucleic acid compound. A preferred method utilizes mammalian cells as the host cells. A more preferred method further utilizes COS-7 mammalian cells. A more preferred method further comprises a DNA vector. In a most preferred method, a DNA vector comprises SEQ ID NO:2 or functional equivalents thereof.

Additionally, a method for expressing a nucleic acid sequence which encodes SEQ ID NO:1 in a host cell is provided. The method comprises transfecting host cells with nucleic acids of the present invention and culturing the transfected host cells under conditions suitable for gene expression. A preferred method utilizes mammalian cells as the host cells. A more preferred method utilizes COS-7 mammalian cells. An even more preferred method utilizes a DNA vector. A most preferred method utilizes both COS-7 cells and a DNA vector comprising SEQ ID NO:2 or functional equivalents thereof.

The methods provided also include those which utilize oocytes as the host cell. Preferably, a method utilizing oocytes also utilizes sense mRNA.

DETAILED DESCRIPTION OF THE INVENTION

The present invention provides compounds which comprises the amino acid sequence SEQ ID NO:1 and functional equivalents thereof. The preferred amino acid compound is SEQ ID NO:1, which is the following sequence of amino acids:

```
Met Gln Lys Ile Met His Ile Ser Val Leu Leu Ser Pro Val Leu Trp
 1               5                  10                   15

Gly Leu Ile Phe Gly Val Ser Ser Asn Ser Ile Gln Ile Gly Gly Leu
             20              25               30

Phe Pro Arg Gly Ala Asp Gln Glu Tyr Ser Ala Phe Arg Val Gly Met
             35              40              45

Val Gln Phe Ser Thr Ser Glu Phe Arg Leu Thr Pro His Ile Asp Asn
         50              55              60

Leu Glu Val Ala Asn Ser Phe Ala Val Thr Asn Ala Phe Cys Ser Gln
 65              70              75              80

Phe Ser Arg Gly Val Tyr Ala Ile Phe Gly Phe Tyr Asp Lys Lys Ser
                 85              90              95

Val Asn Thr Ile Thr Ser Phe Cys Gly Thr Leu His Val Ser Phe Ile
             100             105             110

Thr Pro Ser Phe Pro Thr Asp Gly Thr His Pro Phe Val Ile Gln Met
             115             120             125

Arg Pro Asp Leu Lys Gly Ala Leu Leu Ser Leu Ile Glu Tyr Tyr Gln
     130             135             140

Trp Asp Lys Phe Ala Tyr Leu Tyr Asp Ser Asp Arg Gly Ley Ser Thr
145                 150             155                 160

Leu Gln Ala Val Leu Asp Ser Ala Ala Glu Lys Lys Trp Gln Val Thr
                 165             170             175

Ala Ile Asn Val Gly Asn Ile Asn Asn Asp Lys Lys Asp Glu Met Tyr
             180             185             190

Arg Ser Leu Phe Gln Asp Leu Glu Leu Lys Lys Glu Arg Arg Val Ile
     195             200             205

Leu Asp Cys Glu Arg Asp Lys Val Asn Asp Ile Val Asp Gln Val Ile
     210             215             220

Thr Ile Gly Lys His Val Lys Gly Tyr His Tyr Ile Ile Ala Asn Leu
225             230             235             240

Gly Phe Thr Asp Gly Asp Leu Leu Lys Ile Gln Phe Gly Gly Ala Asn
             245             250             255

Val Ser Gly Phe Gln Ile Val Asp Tyr Asp Asp Ser Leu Val Ser Lys
             260             265             270

Phe Ile Glu Arg Trp Ser Thr Leu Glu Glu Lys Glu Tyr Pro Gly Ala
             275             280             285
```

```
His Thr Thr Thr Ile Lys Tyr Thr Ser Ala Leu Thr Tyr Asp Ala Val
    290                 295                 300

Gln Val Met Thr Glu Ala Phe Arg Asn Leu Arg Lys Gln Arg Ile Glu
305                 310                 315                 320

Ile Ser Arg Arg Gly Asn Ala Gly Asp Cys Leu Ala Asn Pro Ala Val
                325                 330                 335

Pro Trp Gly Gln Gly Val Glu Ile Glu Arg Ala Leu Lys Gln Val Gln
            340                 345                 350

Val Glu Gly Leu Ser Gly Asn Ile Lys Phe Asp Gln Asn Gly Lys Arg
                355                 360                 365

Ile Asn Tyr Thr Ile Asn Ile Met Glu Leu Lys Thr Asn Gly Pro Arg
        370                 375                 380

Lys Ile Gly Tyr Trp Ser Glu Val Asp Lys Met Val Thr Leu Thr
385                 390                 395                 400

Glu Leu Pro Ser Gly Asn Asp Thr Ser Gly Leu Glu Asn Lys Thr Val
                405                 410                 415

Val Val Thr Thr Ile Leu Glu Ser Pro Tyr Val Met Met Lys Lys Asn
            420                 425                 430

His Glu Met Leu Glu Gly Asn Glu Arg Tyr Glu Gly Tyr Cys Val Asp
        435                 440                 445

Leu Ala Ala Glu Ile Ala Lys His Cys Gly Phe Lys Tyr Lys Leu Thr
    450                 455                 460

Ile Val Gly Asp Gly Lys Tyr Gly Ala Arg Asp Ala Asp Thr Lys Ile
465                 470                 475                 480

Trp Asn Gly Met Val Gly Glu Leu Val Tyr Gly Lys Ala Asp Ile Ala
                485                 490                 495

Ile Ala Pro Leu Thr Ile Thr Leu Val Arg Glu Glu Val Ile Asp Phe
            500                 505                 510

Ser Lys Pro Phe Met Ser Leu Gly Ile Ser Ile Met Ile Lys Lys Pro
        515                 520                 525

Gln Lys Ser Lys Pro Gly Val Phe Ser Phe Leu Asp Pro Leu Ala Tyr
    530                 535                 540

Glu Ile Trp Met Cys Ile Val Phe Ala Tyr Ile Gly Val Ser Val Val
545                 550                 555                 560

Leu Phe Leu Val Ser Arg Phe Ser Pro Tyr Glu Trp His Thr Glu Glu
                565                 570                 575

Phe Glu Asp Gly Arg Glu Thr Gln Ser Ser Glu Ser Thr Asn Glu Phe
            580                 585                 590

Gly Ile Phe Asn Ser Leu Trp Phe Ser Leu Gly Ala Phe Met Arg Gln
        595                 600                 605

Gly Cys Asp Ile Ser Pro Arg Ser Leu Ser Gly Arg Ile Val Gly Gly
    610                 615                 620

Val Trp Trp Phe Phe Thr Leu Ile Ile Ile Ser Ser Tyr Thr Ala Asn
625                 630                 635                 640

Leu Ala Ala Phe Leu Thr Val Glu Arg Met Val Ser Pro Ile Glu Ser
                645                 650                 655

Ala Glu Asp Leu Ser Lys Gln Thr Glu Ile Ala Tyr Gly Thr Leu Asp
            660                 665                 670

Ser Gly Ser Thr Lys Glu Phe Phe Arg Arg Ser Lys Ile Ala Val Phe
        675                 680                 685

Asp Lys Met Trp Thr Tyr Met Arg Ser Ala Glu Pro Ser Val Phe Val
    690                 695                 700

Arg Thr Thr Ala Glu Gly Val Ala Arg Val Arg Lys Ser Lys Gly Lys
```

-continued

```
705                     710                     715                     720
Tyr Ala Tyr Leu Leu Glu Ser Thr Met Asn Glu Tyr Ile Glu Gln Arg
                    725                     730                     735

Lys Pro Cys Asp Thr Met Lys Val Gly Gly Asn Leu Asp Ser Lys Gly
                740                     745                     750

Tyr Gly Ile Ala Thr Pro Lys Gly Ser Ser Leu Arg Thr Pro Val Asn
            755                     760                     765

Leu Ala Val Leu Lys Leu Ser Glu Gln Gly Val Leu Asp Lys Leu Lys
        770                     775                     780

Asn Lys Trp Trp Tyr Asp Lys Gly Glu Cys Gly Ala Lys Asp Ser Gly
785                     790                     795                     800

Ser Lys Glu Lys Thr Ser Ala Leu Ser Leu Ser Asn Val Ala Gly Val
                805                     810                     815

Phe Tyr Ile Leu Val Gly Gly Leu Gly Leu Ala Met Leu Val Ala Leu
                820                     825                     830

Ile Glu Phe Cys Tyr Lys Ser Arg Ala Glu Ala Lys Arg Met Lys Val
            835                     840                     845

Ala Lys Asn Ala Gln Asn Ile Asn Pro Ser Ser Ser Gln Asn Ser Gln
        850                     855                     860

Asn Phe Ala Thr Tyr Lys Glu Gly Tyr Asn Val Tyr Gly Ile Glu Ser
865                     870                     875                     880

Val Lys Ile.
```

Those in the art will recognize that some alterations of SEQ ID NO:1 will fail to change the function of the compound. For instance, some hydrophobic amino acids may be exchanged for other hydrophobic amino acids. Those altered compounds which confer the function of SEQ ID NO:1 in substantially the same manner as the exemplified compound are also included in the present invention.

Artisans will also recognize that these compounds can be synthesized by a number of different methods. All of the amino acid compounds of the invention can be made by chemical methods well known in the art, including solid phase peptide synthesis or recombinant methods. Both methods are described in U.S. Pat. No. 4,617,149. Recombinant methods are preferred if a high yield is desired. A general method for the construction of any desired DNA sequence is provided in Brown et al., 68 Methods in Enzymology 109 (1979).

Other routes of production are well known to those in the art. Expression in eucaryotic cells can be achieved via SEQ ID NO:2. For example, the amino acid compounds can be produced in eucaryotic cells using SV40-derived expression vectors comprising DNA which encodes for SEQ ID NO:1.

As is well known in the art, some viruses are also appropriate vectors. For example, the adenoviruses, the papovaviruses, the vaccinia viruses, the herpes viruses, and the baculoviruses, as well as vectors derived from these viruses, are useful. Such a method is described in U.S. Pat. No. 4,775,624. Several alternate methods of expression are described in J. Sambrook, E. F. Fritsch & T. Maniatis, *Molecular Cloning: A Laboratory Manual* 16.3–17.44 (1989) and *Methods in Enzymology*, Vol. 185 (1990).

Other embodiments of the present invention are nucleic acid compounds which comprise nucleic acid sequences which encode all or part of SEQ ID NO:1 or functional equivalents thereof. As artisans will recognize, the amino acid compounds of the invention can be encoded by a multitude of different nucleic acid sequences because most of the amino acids are encoded by more than one nucleic acid triplet. Because these alternate nucleic acid sequences would encode substantially the same amino acid sequence, the present invention further comprises these alternate nucleic acid sequences. Preferably, the nucleic acid compound is DNA or sense mRNA. A most preferred embodiment of a DNA compound encoding the HSG1uR2 compound has this sequence:

```
ATGCAAAAGA TTATGCATAT TTCTGTCCTC CTTTCTCCTG TTTTATGGGG ACTGATTTTT    60
GGTGTCTCTT CTAACAGCAT ACAGATAGGG GGGCTATTTC CTAGGGGCGC CGATCAAGAA   120
TACAGTGCAT TTCGAGTAGG GATGGTTCAG TTTTCCACTT CGGAGTTCAG ACTGACACCC   180
CACATCGACA ATTTGGAGGT GGCAAACAGC TTCGCAGTCA CTAATGCTTT CTGCTCCCAG   240
TTTTCGAGAG GAGTCTATGC TATTTTTGGA TTTTATGACA AGAAGTCTGT AAATACCATC   300
ACATCATTTT GCGGAACACT CCACGTCTCC TTCATCACTC CCAGCTTCCC AACAGATGGC   360
ACACATCCAT TTGTCATTCA GATGAGACCC GACCTCAAAG GAGCTCTCCT TAGCTTGATT   420
```

-continued

```
GAATACTATC AATGGGACAA GTTTGCATAC CTCTATGACA GTGACAGAGG CTTATCAACA    480

CTGCAAGCTG TGCTGGATTC TGCTGCTGAA AAGAAATGGC AAGTGACTGC TATCAATGTG    540

GGAAACATTA ACAATGACAA GAAAGATGAG ATGTACCGAT CACTTTTTCA AGATCTGGAG    600

TTAAAAAAGG AACGGCGTCT AATTCTGGAC TGTCAAAGGG ATAAACTAAA CGACATTGTA    660

GACCAGGTTA TTACCATTGG AAAACATGTT AAAGGGTACC ACTACATCAT TGCAAATCTG    720

GGATTTACTG ATGGAGACCT ATTAAAAATC CAGTTTGGAG GTGCAAATGT CTCTGGATTT    780

CAGATAGTGG ACTATGATGA TTCGTTGGTA TCTAAATTTA TAGAAAGATG GTCAACACTG    840

GAAGAAAAAG AATACCCTGG AGCTCACACA ACAACAATTA AGTATACTTC TGCTCTGACC    900

TATCATGCCG TTCAAGTGAT GACTGAAGCC TTCCGCAACC TAAGGAAGCA AAGAATTGAA    960

ATCTCCCGAA GGGGGAATGC AGGAGACTGT CTGGCAAACC CAGCAGTGCC CTGGGGACAA   1020

GGTGTAGAAA TAGAAAGGGC CCTCAAACAG GTTCAGGTTG AAGGTCTCTC AGGAAATATA   1080

AAGTTTGACC AGAATGGAAA AAGAATAAAC TATACAATTA ACATCATGGA GCTCAAAACT   1140

AATGGGCCCC GGAAGATTGG CTACTGGAGT GAAGTGGACA AAATGGTTGT TACCCTTACT   1200

GAGCTCCCTT CTGAAATGA CACCTCTGGG CTTGAGAATA AGACTGTTGT TGTCACCACA   1260

ATTTTGGAAT CTCCGTATGT TATGATGAAG AAAAATCATG AAATGCTTGA AGGCAATGAG   1320

CGCTATGAGG GCTACTGTGT TGACCTGGCT GCAGAAATCG CCAAACATTG TGGGTTCAAG   1380

TACAAGTTGA CAATTGTTGG TGATGGCAAG TATGGGCCA GGGATGCAGA CACGAAAATT    1440

TGGAATGGGA TGGTTGGAGA ACTTGTATAT GGGAAAGCTG ATATTGCAAT TGCTCCATTA   1500

ACTATTACCC TTGTGAGAGA AGAGGTGATT GACTTCTCAA AGCCCTTCAT GAGCCTCGGG   1560

ATATCTATCA TGATCAAGAA GCCTCAGAAG TCCAAACCAG GAGTGTTTTC CTTTCTTGAT   1620

CCTTTAGCCT ATGAGATCTG GATGTGCATT GTTTTTGCCT ACATTGGGGT CAGTGTAGTT   1680

TTATTCCTGG TCAGCAGATT TAGCCCCTAC GAGTGGCACA CTGAGGAGTT TGAAGATGGA   1740

AGAGAAACAC AAAGTAGTGA ATCAACTAAT GAATTTGGGA TTTTTAATAG TCTCTGGTTT   1800

TCCTTGGGTG CCTTTATGCG GCAAGGATGC GATATTTCGC CAAGATCCCT CTCTGGGCGC   1860

ATTGTTGGAG GTGTGTGGTG GTTCTTTACC CTGATCATAA TCTCCTCCTA CACGGCTAAC   1920

TTAGCTGCCT TCCTGACTGT AGAGAGGATG GTGTCTCCCA TCGAAAGTGC TGAGGATCTT   1980

TCTAAGCAAA CAGAAATTGC TTATGGAACA TTAGACTCTG GCTCCACTAA AGAGTTTTTC   2040

AGGAGATCTA AAATTGCAGT GTTTGATAAA ATGTGGACCT ACATGCGGAG TGCGGAGCCC   2100

TCTGTGTTTG TGAGGACTAC GGCCGAAGGG GTGGCTAGAG TGCGGAAGTC CAAAGGGAAA   2160

TATGCCTACT TGTTGGAGTC CACGATGAAC GAGTACATTG AGCAAAGGAA GCCTTGCGAC   2220

ACCATGAAAG TTGGTGGAAA CCTGGATTCC AAAGGCTATG GCATCGCAAC ACCTAAAGGA   2280

TCCTCATTAA GAACCCCAGT AAATCTTGCA GTATTGAAAC TCAGTGAGCA AGGCGTCTTA   2340

GACAAGCTGA AAAACAAATG GTGGTACGAT AAAGGTGAAT GTGGAGCCAA GGACTCTGGA   2400

AGTAAGGAAA AGACCAGTGC CCTCAGTCTG AGCAACGTTG CTGGAGTATT CTACATCCTT   2460

GTCGGGGCC TTGGTTTGGC AATGCTGGTG GCTTTGATTG AGTTCTGTTA CAAGTCAAGG   2520

GCCGAGGCGA AACGAATGAA GGTGGCAAAG AATGCACAGA ATATTAACCC ATCTTCCTCG   2580

CAGAATTCAC AGAATTTTGC AACTTATAAG GAAGGTTACA ACGTATATGG CATCGAAAGT   2640

GTTAAAATT.                                                           2649
```

This is the sequence identified as SEQ ID NO:2.

E. coli/pRS113, which contains a cloning vector comprising SEQ ID NO:2, was deposited and made part of the stock culture collection of the Northern Regional Research Laboratories (NRRL), Agricultural Research Service, U.S. Department of Agriculture, Peoria, Ill., 61604 on Apr. 22, 1992, under the accession nu ber NRRL B-18968. SEQ ID NO:2 can be isolated from the plasmid, for example, as an approximately 2.9 kb AlwnI/SalI restriction fragment. Other fragments are also useful in obtaining SEQ ID NO:2.

Additionally, the DNA sequences can be synthesized using automated DNA synthesizers, such as the ABS (Applied Biosystems, 850 Lincoln Centre Drive, Foster City, Calif. 94404) 380B DNA synthesizer. The DNA sequences can also be generated by the polymerase chain reaction (PCR) as described in U.S. Pat. No. 4,889,818.

Because those in the art will recognize that many vectors are available for expression and cloning, those expression and cloning vectors which comprise nucleic acids which encode SEQ ID NO:1 or functional equivalents thereof are included in the present invention. The preferred nucleic acid vectors are those which are DNA. Most preferred are DNA vectors which comprise the DNA sequence which is SEQ ID NO:2. The DNA vector most preferred is plasmid pRS113.

Restriction fragments of these vectors are also provided. The preferred fragments are the approximately 2.9 kb AlwnI/SalI restriction fragment and the approximately 2.9 kb EcoRI restriction fragment of pRS113.

DNA vectors which further comprise a promoter positioned to drive expression of HSG1uR2 receptor are also provided. Preferred DNA expression vectors are those wherein the promoter functions in mammalian cells. More preferred DNA expression vectors are those wherein the promoter functions in COS-7 cells. Most preferred COS-7 DNA expression vectors comprise SEQ ID NO:2.

Plasmid pRS113 may be isolated from the deposited *E. coli*/pRS113, using an ordinary cesium chloride DNA isolation procedure. Plasmid pRS113 can be readily utilized to construct expression vectors which produce HSG1uR2 receptors in a variety of organisms and cell lines, including, for example, CV1 cells, COS cells, CHO cells, *E. coli*, Sf9 (as host for baculovirus), Pichia and Saccharomycetes. The current literature contains techniques for constructing expression vectors and for transfecting host cells. For example, Sambrook et al., *Molecular Cloning: A Laboratory Manual* Chapters 16 and 17 (1989), explains these techniques.

The construction protocols discussed in Sambrook et al. can be followed to construct analogous vectors for other organisms merely by substituting, if necessary, the appropriate regulatory elements using techniques well known to artisans. Promoters which may be used, for example, are the thymidine kinase promoter, the metallothionin promoter or various viral and immmunoglobulin promoters.

The DNA compounds of the present invention also include primers or probes. Nucleic acid compounds of at least 18 base pairs which encode all or a part of SEQ ID NO:1 are included in the present invention. DNA is the preferred nucleic acid used as a probe or primer. Most preferred DNA compounds useful as probes or primers are: SEQ ID NO:3, SEQ ID NO:4 and SEQ ID NO:5. Those in the art will recognize the techniques associated with probes and primers as well known. Any sequence of at least 18 consecutive base pairs in length of the nucleic acids of the present invention may be used to screen any other nucleic acid. For example, all or part of SEQ ID NO:3 and all or part of the reverse complement of SEQ ID NO:5 may be used to hybridize to the terminal ends of the coding sequence. Then, through PCR amplification, the full length sequence may be generated. The full length sequence can be subsequently subcloned into any vector of choice.

Alternatively, SEQ ID NO:3, SEQ ID NO:4, or SEQ ID NO:5 may be radioactively labeled at the 5' end in order to screen cDNA libraries by conventional means. Furthermore, any piece of HSG1uR2 DNA which has been bound to a filter may be flooded with total mRNA transcripts, in order to then reverse-transcribe the mRNA transcripts which bind.

Primers and probes may be obtained by means well known in the art. For example, once pRS113 is isolated, restriction enzymes and subsequent gel separation may be used to isolate the fragment of choice.

Host cells which harbor the nucleic acids provided by the present invention are also provided. For example, oocytes which comprise nucleic acids of the present invention are provided. Oocytes wherein the nucleic acid is DNA are preferred. Also preferred are oocytes wherein the nucleic acid harbored is sense mRNA.

Furthermore, oocytes which harbor nucleic acids encoding functional HSG1uR2 receptor are provided. Oocytes which harbor nucleic acids capable of expressing functional HSG1uR2/HSG1uR1 complex are also provided by the present invention. oocytes which, in addition to harboring nucleic acids capable of expressing functional HSG1uR2/HSG1uR1 complex, further harbor nucleic acids capable of expressing GluR3 receptor are also provided.

Moreover, oocytes which comprise vectors encoding functional HSG1uR2 and which further comprise vectors encoding GluR1 receptor are provided. Likewise, oocytes which comprise vectors encoding functional HSG1uR2 receptor and which further comprise vectors encoding GluR3 receptor are provided. Furthermore, oocytes which comprise vectors encoding functional HSG1uR2 receptor, along with vectors encoding GluR1 receptor and vectors encoding GluR3 receptor are also provided. Most preferred oocytes of the present invention are those which harbor sense mRNA.

Host cells provided also include those comprising a nucleic acid vector which encodes SEQ ID NO:1. Preferred are those host cells wherein the nucleic acid vector is DNA. Most preferred are host cells wherein the DNA vector comprises the DNA sequence SEQ ID NO:2. Preferred host cells include *E. coli* cells. The most preferred *E. coli* cell is one transfected with plasmid pRS113.

Host cells which are transfected with a DNA expression vector which encodes HSG1uR2 receptor are also provided. Preferably, the DNA vector comprises SEQ ID NO:2. Preferred host cells for expression of functional HSG1uR2 are mammalian cells. Preferred mammalian cells for expression of HSG1uR2 are COS-7 cells.

Host cells which are transfected with DNA expression vectors encoding HSG1uR2/HSG1uR1 complex are also provided. Host cells which have been transfected with a DNA expression vector which expresses functional HSG1uR2/HSG1uR1 complex and which further comprise a vector which encodes a GluR3 receptor are also provided. Host cells which comprise a DNA expression vector encoding HSG1uR2 and which further comprise a vector encoding GluR1 receptor are also part of the invention. Furthermore, host cells which comprise a DNA expression vector encoding HSG1uR2 and which further comprise a vector encoding GluR3 receptor are also provided. Host cells which (a) have been transfected with a DNA expression vector which expresses HSG1uR2 receptor, and (b) further comprise a vector which encodes a GluR1 receptor, and (c) further comprise a vector which encodes a GluR3 receptor are also provided. Wigler M. et al., 16 *Cell* 777 (1979), describe such a cotransfection procedure.

Oocytes harboring foreign nucleic acids can be constructed according to the procedures described in Lübbert, et al. 84 *Proc. Nat. Acad. Sci.* 4332 (1987) and Berger, *Meth-*

*ods in Enzymology*, Vol. 152 (1987). Other host cell transfection procedures are well known in the art. Nucleic acids which encode HSG1uR1 can be obtained from NRRL, under accession number B-118967. Nucleic acids which encode GluR2 and GluR3 can be obtained according to Heinemann S. et al., PCT publication WO91/06648 (1992).

Additionally, the invention provides a method for identifying DNA homologous to a probe of the present invention, which comprises contacting test nucleic acid with the probe under hybridizing conditions and identifying those nucleic acids which hybridize. The preferred probes for use in this method are SEQ ID NO:3, SEQ ID NO:4 or SEQ ID NO:5. Hybridization techniques are well known in the art. Sambrook et al., *Molecular Cloning: A Laboratory Manual* 11 (1989) describe such procedures.

Assays utilizing the compounds provided by the present invention are also provided. Assays provided include a method for determining whether a substance interacts with or affects HSG1uR2, said method comprising introducing said substance and functional HSG1uR2 into an acceptable medium, and monitoring interaction by physically detectable means, thereby identifying those substances which interact with or affect HSG1uR2. Still other assays further utilize a HSG1uR1 receptor. Other assays utilize both functional HSG1uR2/HSG1uR1 complex and GluR3. Assays also include those which utilize both HSG1uR2 and GluR1 receptor. Likewise, assays include those which utilize HSG1uR2 and GluR3 receptor. Another assay utilizes HSG1uR2, GluR1 and GluR3.

Preferably, the physically detectable means is selected from 1) competing with labeled glutamate, 2) interacting with glutaminergic ligand or 3) generating ion flow. A most preferred competition assay utilizes radioactively labeled glutamate.

A preferred assay is an oocyte assay system. A most preferred oocyte assay system utilizes sense mRNA. Most preferred is an assay wherein the oocyte expression system utilizes sense mRNA.

The oocyte expression system can be constructed according to the procedure described in Lübbert, et al. 84 *Proc. Nat. Acad. Sci.* 4332 (1987) and Berger, *Methods in Enzymology*, Vol.152 (1987). The radiolabeled glutamate competition assay may be accomplished according to Foster and Fagg, 7 *Brain Res. Rev.* 103 (1984). The assay which measures ion flow may be accomplished according to Hamill O. P. et al., 391 (No. 2) Pflugers Archiv:European J. of Physiology, 85 (1981).

Artisans will recognize that competition assays results are described in terms of $K_i$ values and artisans realize that desirable $K_i$ values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention provides assays which indicate whether a substance has either a high affinity or low affinity to HSG1uR2 receptor.

The present invention also provides a method for constructing a host cell capable of expressing SEQ ID NO:1 or functional equivalents thereof, said method comprising transfecting a host cell with a DNA vector that comprises a DNA sequence which encodes SEQ ID NO:1 or functional equivalents thereof. A general method for the construction of any desired DNA sequence is provided in Brown et al., 68 *Methods in Enzymology* 109 (1979).

A preferred method utilizes mammalian cells as host cells. Preferably, the maalian cells utilized are for this method are COS-7 cells. An especially preferred method utilizes a DNA expression vector in COS-7 cells. An even more preferred method utilizes a DNA expression vector which comprises SEQ ID NO:2 or functional equivalents thereof. Transfected host cells may be cultured under conditions well known to those in the art such that SEQ ID NO:1 is expressed, thus producing HSG1uR2 in the host cell.

Therefore, also provided by the present invention is a method for expressing a gene which encodes SEQ ID NO:1 in a transfected host cell, said method comprising culturing said transfected host cell under conditions suitable for gene expression. A preferred method utilizes mammalian cells. A most preferred method utilizes COS-7 cells. A more preferred method utilizes COS-7 cells as host cells for a DNA vector. A most preferred method utilizes COS-7 cells as host cells for a DNA vector comprising SEQ ID NO:2. Another method utilizes oocytes as the host cells. Methods wherein oocytes are utilized preferably expresses sense mRNA. Expression in host cells may be accomplished according to the procedures outlined in Sambrook et al., *Molecular Cloning: A Laboratory Manual* 16–17 (1989).

The following are examples of the present invention:

EXAMPLE 1

Growth of *E. coli*/pRS113

A lyophilized culture of *E. coli* containing plasmid pRS113 can be obtained from the American Type Culture Collection, Rockville, Md. 20852, and inoculated into a suitable broth for the growth of *E. coli* using standard microbiological procedures.

The contents of a lyophil vial containing *E. coli*/pRS113 were transferred into 100 ml of sterile YT (tryptone-yeast extract) broth containing 100 μg/ml ampicillin in a one liter fermentation flask and shaken at 37° C. on an orbital shaker at 250–300 rpm. After the optical density (OD, measured at 600 millimicrons) had reached approximately 1–2 OD, the bacterial cells were recovered and used for the isolation of plasmid pRS113 according to the procedures detailed in J. Sambrook et al., *Molecular Cloning*, Chapter 1, (1989).

Once isolated from the bacterial cells, the plasmid DNA served as a source for the DNA encoding the human HSG1uR2 receptor protein. One convenient method to remove the receptor-encoding DNA from plasmid pRS113 was to digest the plasmid with restriction enzymes AlwnI and SalI. These enzymes cut the plasmid at unique sites to produce a DNA fragment of approximately 2.9 kb containing the entire coding sequence of the human HSG1uR2 receptor.

EXAMPLE 2

In Vitro Transcription of RNA using pRS113 as a DNA Template

RNA transcripts encoding the HSG1uR2 receptor were produced by enzymatic transcription from pRS113 using an RNA polymerase which recognizes the transcription promoter contained in the plasmid adjacent to the amino terminal coding end of the receptor subunit cDNA. Plasmid pRS113 was treated with the restriction enzyme SalI which made a single cut distal to the 3' end of the cDNA insert in the circular DNA and converted the plasmid DNA into a linear form. This DNA was then incubated with T7 RNA polymerase in the presence of GpppG cap nucleotide, rATP, rCTP, rUTP and rGTP. The synthetic RNA transcript obtained was purified by passage over a Sephadex G-50 column. For a detailed description of in vitro RNA synthesis using bacteriophage RNA polymerase such as T7, see P. A. Krieg and D. A. Melton, Vol 155, *Methods in Enzymology*, Ch. 25, 1987.

EXAMPLE 3

Functional Expression of Human HSG1uR2 Receptor in Xenopus Oocytes

Oocytes suitable for injection were obtained from the adult female Xenopus laevis using procedures described in C. J. Marcus-Sekura and M. J. M. Hitchcock, *Methods in Enzymology*, Vol. 152 (1987). After treatment with collagenase type la (Sigma) at a concentration of 2 mg/ml, the defolliculated oocytes were injected essentially as described by M. J. M. Hitchcock et al., *Methods in Enzymology*, Vol. 152 Chapter 28, (1987). Subsequently, 5–10 ng of RNA transcript in a total volume of 50 nl, prepared as described in Example 2, were injected into each oocyte and they were then incubated in Barth's saline solution at 18° C. until needed for electrophysiological measurements.

In order to detect the presence of HSG1uR2 receptor, the ability of the receptor to assemble into functional ion channels was determined by voltage recording of electrical current flowing across the oocyte membrane in response to glutamate agonists. Individual oocytes were placed in a diffusion chamber (0.5 ml vol.) through which solutions were perfused rapidly. Drugs (agonists and antagonists) were applied to the oocytes by adding them to the perfusing solutions and subsequently washing them out with control solution. The control solution contained 96 mM NaCl, 2 mM KCl, 1.8 mM CaCl2, 1 mM MgCl2, and 5 mM HEPES buffer, pH 7.6. After insertion of electrodes into the oocytes, voltage recordings were made using the bridge circuit of an Axoclamp 1A voltage-clamp unit. Microelectrodes were filled with 3 M CsCl. Electrophysiological recordings of the oocytes clamped at −70 mV were made at room temperature (20–25° C.), 3 days or more after injection of RNA into the oocytes. In response to perfusion of the cells with 1 mM L-glutamate, inward currents across the oocyte membrane of 3 to 5 nanoamperes was observed. When RNA transcripts (5 ng each) which encoded both HSG1uR2 and HSG1uR1 were coinjected, currents of approximately 70 nanoamperes were observed in response to perfusion with 40 $\mu$M kainic acid. For a detailed discussion of the electrophysiology of xenopus oocytes see Dascal N., 22 *CRC Critical Reviews in Biochemistry*, 317 (1987). As those skilled in the art appreciate these results are indicative of a glutamate receptor.

We claim:

1. An isolated and purified nucleic acid compound which comprises a nucleic acid sequence which encodes the compound of SEQ ID NO:1.

2. A compound of claim 1 which is DNA.

3. A DNA compound of claim 2 which is SEQ ID NO:2.

4. A nucleic acid vector which comprises a nucleic acid compound of claim 1.

5. A nucleic acid vector of claim 4 which is DNA.

6. A DNA vector of claim 5 which comprises the DNA sequence SEQ ID NO:2.

7. The DNA vector of claim 6 which is pRS113.

* * * * *